(12) United States Patent
Hautvast et al.

(10) Patent No.: US 10,603,114 B2
(45) Date of Patent: Mar. 31, 2020

(54) METHOD AND SYSTEM FOR DETECTING A FAST MOVING SURGICAL DEVICE

(71) Applicant: KONINKLIJKE PHILIPS N.V., Eindhoven (NL)

(72) Inventors: Guillaume Leopold Theodorus Frederik Hautvast, Veldhoven (NL); Gernot Joseph Pieter Marie Eggen, Oosterhout (NL)

(73) Assignee: Koninklijke Philips N.V., Eindhoven (NL)

( * ) Notice: Subject to any disclaimer, the term of this patent is extended or adjusted under 35 U.S.C. 154(b) by 525 days.

(21) Appl. No.: 15/301,435

(22) PCT Filed: Apr. 8, 2015

(86) PCT No.: PCT/EP2015/057555
§ 371 (c)(1),
(2) Date: Oct. 3, 2016

(87) PCT Pub. No.: WO2015/158577
PCT Pub. Date: Oct. 22, 2015

(65) Prior Publication Data
US 2017/0035515 A1 Feb. 9, 2017

(30) Foreign Application Priority Data
Apr. 17, 2014 (EP) .................................... 14165081

(51) Int. Cl.
*A61B 34/20* (2016.01)
*A61B 34/10* (2016.01)
*A61B 10/02* (2006.01)

(52) U.S. Cl.
CPC .......... *A61B 34/20* (2016.02); *A61B 10/0275* (2013.01); *A61B 2010/0208* (2013.01); *A61B 2034/107* (2016.02); *A61B 2034/2051* (2016.02)

(58) Field of Classification Search
CPC ................ A61B 34/20; A61B 10/0275; A61B 2034/2051; A61B 10/02–06; A61B 2010/0208–045; G05B 2219/32092
(Continued)

(56) References Cited

U.S. PATENT DOCUMENTS 5,595,185 A 1/1997 Erlich
5,673,210 A * 9/1997 Etter .................. G11B 20/1876
702/69

(Continued)

FOREIGN PATENT DOCUMENTS

JP 2001524339 A 12/2001
WO WO-2012098483 A1 * 7/2012 ........... A61B 8/0481

*Primary Examiner* — Patricia J Park
*Assistant Examiner* — Victoria Fang

(57) ABSTRACT

The present invention proposes an electromagnetic (EM) tracking technology that can be used to track devices with embedded EM sensors over time. If these objects move too fast, tracking signals are lost because of the motion induced potential differences. It is therefore proposed to add a processing mechanism incorporating additional processing algorithms to enable tracking of the EM sensors. An embodiment of the invention is for performing biopsies using a biopsy gun. The additional processing algorithms incorporate dedicated prior information on the expected signal obtained from the embedded EM sensor and are introduced to allow processing the signals from the moving sensors. The prior information can be incorporated in a heuristic or statistical model to process the EM signal.

16 Claims, 3 Drawing Sheets

(58) Field of Classification Search
USPC .......................................................... 600/424
See application file for complete search history.

(56) References Cited

U.S. PATENT DOCUMENTS

| | | | |
|---|---|---|---|
| 5,961,553 | A | 10/1999 | Coty et al. |
| 7,876,268 | B2 | 1/2011 | Jacobs |
| 8,170,830 | B2 | 5/2012 | Jacobs |
| 8,216,153 | B2 | 7/2012 | Fischer et al. |
| 8,401,616 | B2 | 3/2013 | Verard et al. |
| 8,457,382 | B2 | 6/2013 | Sebok |
| 8,512,219 | B2 | 8/2013 | Ferren et al. |
| 8,600,106 | B1* | 12/2013 | Parenteau ............... G06T 7/246 382/103 |
| 8,652,124 | B2 | 2/2014 | Wiksell et al. |
| 9,554,812 | B2 | 1/2017 | Inkpen et al. |
| 2003/0043073 | A1* | 3/2003 | Gray .................... G01S 5/0215 342/465 |
| 2004/0097805 | A1* | 5/2004 | Verard ............... A61B 1/00071 600/428 |
| 2007/0081096 | A1 | 4/2007 | Gunnewick et al. |
| 2008/0083414 | A1 | 4/2008 | Messerges |
| 2008/0114235 | A1* | 5/2008 | Unal .................... G01R 33/286 600/411 |
| 2009/0027051 | A1* | 1/2009 | Stuber ................ G01R 33/4828 324/309 |
| 2010/0210939 | A1 | 8/2010 | Hartmann et al. |
| 2011/0243309 | A1 | 10/2011 | Weijiang |
| 2012/0083702 | A1* | 4/2012 | Ingold, Jr. .............. A61B 5/061 600/483 |
| 2012/0095330 | A1* | 4/2012 | Shechter .................. A61B 5/06 600/424 |
| 2013/0289393 | A1 | 10/2013 | Kruecker et al. |
| 2013/0296737 | A1 | 11/2013 | McMillan et al. |
| 2013/0338477 | A1* | 12/2013 | Glossop ............. A61B 10/0241 600/407 |
| 2013/0345718 | A1* | 12/2013 | Crawford ............ A61B 17/025 606/130 |
| 2014/0148808 | A1* | 5/2014 | Inkpen ................... G01B 7/003 606/80 |
| 2014/0257080 | A1* | 9/2014 | Dunbar ................ A61B 8/4416 600/409 |

\* cited by examiner

METHOD AND SYSTEM FOR DETECTING A FAST MOVING SURGICAL DEVICE

CROSS-REFERENCE TO PRIOR APPLICATIONS

This application is the U.S. National Phase application under 35 U.S.C. § 371 of International Application Serial No. PCT/EP2015/057555, filed on Apr. 8, 2015, which claims the benefit of European Patent Application No. 14165081.2, filed on Apr. 17, 2014. These applications are hereby incorporated by reference herein.

FIELD OF THE INVENTION

The invention relates to the field of a medical system and a method for detecting a medical device, such as—but not limited—to an electromagnetically tracked biopsy device.

BACKGROUND OF THE INVENTION

Electromagnetic (EM) tracking technology is increasingly being used in the field of image guided interventions and therapy (IGIT).

For instance, EP 1 504 713 A1 discloses an image guided navigation system for navigating a region of a patient, which includes an imaging device, a tracking device, a controller, and a display. The imaging device generates images of the region of a patient. The tracking device makes use of an EM tracking system to track the location of the instrument in a region of the patient and the controller superimposes an icon representative of the instrument onto the images generated from the imaging device based upon the location of the instrument.

EM spatial measurement systems determine the location of medical objects based on electromagnetic induction. Such medical objects are embedded with sensor coils or other EM sensors. When the medical object is placed inside controlled varying magnetic fields, voltages (potential differences) are induced in the EM sensors, e.g., coils. These induced voltages are used by the measurement system to calculate the position and orientation of the medical object.

Unfortunately, electromagnetic induction also occurs when the object is being moved through a static magnetic field. The induced potential difference in this scenario is proportional to the derivative of the magnetic flux, which in turn relates to the speed of relative movement between the medical object and the static magnetic field.

EM spatial measurement systems may determine the location and orientation of objects purely based on observed voltages and thus cannot distinguish between the sources of the potential difference. Thus, the positioning of a medical object in motion is—by definition—less accurate, compared to a static medical object. In most practical applications, this does not cause problems as the induced potential differences due to motion are relatively small compared to the induced potential difference generated by the magnetic field variation. As a result, an introduced measurement error is small compared to the noise of the measurement system.

However, when the movement of the medical object is fast, the additionally induced potential difference does introduce significant errors in positioning. If the motion is very fast, the potential difference may even exceed expected induction levels due to the magnetic field variation. In the latter scenario, EM systems report lost signals from the EM sensor. As a result, EM systems cannot be used for tracking fast moving objects.

SUMMARY OF THE INVENTION

It is an object of the present invention to provide an EM object detection method and system which can be used for detecting fast moving objects.

This object is achieved by a medical system as claimed in claim 1, by a detection method as claimed in claim 14, and by a computer program product as claimed in claim 15.

Thus, according to a first aspect of the present invention, a medical system incorporating an automatic detection system is presented, comprising:

a guidance system having an acceleration mechanism for generating an accelerated movement of a surgical device to drive the surgical device into a tissue of a subject;

an electromagnetic sensor provided on the surgical device;

an electromagnetic spatial measurement system adapted to detect an induced output signal of the electromagnetic sensor and to determine at least one of an orientation and a location of the surgical device and/or an activation of the acceleration mechanism based on the detected output signal;

a signal processing unit adapted to process the detected output signal based on dedicated prior information about the output signal of the electromagnetic sensor that is expected when the acceleration mechanism is activated.

Moreover, according to a second aspect of the present invention, a detection method is presented, comprising:

generating an accelerated movement of a surgical device to drive the surgical device into a tissue of a subject, by using an acceleration mechanism;

detecting an induced output signal of an electromagnetic sensor provided on said surgical device;

determining at least one of an orientation and a location of the surgical device and/or an activation of the acceleration mechanism based on the detected output signal;

processing the detected output signal based on dedicated prior information about the output signal of the electromagnetic sensor that is expected when the acceleration mechanism is activated.

Furthermore, according to a third aspect of the present invention, a computer program product comprising code means for producing the steps of the above method when run on a computer device is presented.

Accordingly, additional signal processing is introduced to allow reconstruction of output signals from fast moving sensors. This additional processing incorporates dedicated prior knowledge on the expected signal obtained from a fast moving EM sensor.

Preferably, the guidance system is a biopsy gun and the surgical device is a trocar (inner needle) and/or a cannula (outer needle) of a biopsy needle. In this case, the acceleration mechanism may be, for instance, a spring-loading mechanism or another acceleration mechanism that drives the trocar and/or the cannula into the tissue of the subject at high speed, such as to preferably reduce deformations and trauma. Alternatively, it is preferred that the surgical device is a needle, for instance, a radiotherapy needle, for placing a therapeutic element, for instance, a radiation source, into the tissue of the subject. In this case, the acceleration mechanism may also be a spring-loading mechanism, a hammering mechanism or another mechanism that drives the needle, for instance, the radiotherapy needle, into the tissue of the subject at high speed, such as to preferably reduce deformations and trauma. In both cases, it is preferred that the acceleration mechanism accelerates the surgical device to a speed of more than 0.75 m/s, preferably, more than 1.5 m/s, most preferably, more than 5.0 m/s.

According to a first option, the output signal may be processed by incorporating the prior information in a heuristic descriptor. The use of the heuristic descriptor allows fast reconstruction of the lost signal or signal portions. In a specific example, the heuristic descriptor may be parameterized to cover at least one class of similar devices. This allows adaptation of the recovery mechanism to the specific type of surgical device on which the EM sensor is provided.

As a specific example of the first option, the output signal may be processed based on at least one of a fact that the output signal is lost, a number of samples that the output signal is lost, a translation distance between location points before and after losing the output signal, and an orientation alignment between the location points before and after losing the output signal. Thereby, information that can be easily derived from the sensor output can be used for reconstructing lost signals or signal portions.

According to a second option which can be combined with the above first option, a user interface or a configuration mechanism may be provided and adapted to allow configuration of parameter values of the heuristic descriptor. Thereby, a user is allowed to modify the heuristic descriptor to optimize system performance.

According to a third option which can be combined with the above first or second option, a statistical model may be generated for the output signal as expected when the acceleration mechanism is activated. This statistical model can be obtained from previous and/or later activations of the acceleration mechanism to allow signal recovery based on recorded system behavior. The statistical model may thus relate to one or more samples of the output signal before and after the output signal, including the lost samples. More specifically, the output signal may be recorded a plurality of times in response to the activation of the acceleration mechanism so as to compute the statistical model. Thus, a reliable statistical model or descriptor can be obtained from previous system operations.

According to a fourth option which can be combined with the above third option, a training user interface may be provided for modifying the statistical model in accordance with different types of the surgical device. This allows individual adaptation of the system to various types of surgical devices based on user preferences.

According to a fifth option which can be combined with any one of the above first to fourth options, the output signal may be processed based on a previously defined motion pattern. Thus, the prior information can be obtained by evaluating previous motion behavior, e.g., so as to fill in missing samples. As a specific example of the fifth embodiment, a lost sensor output signal can be reconstructed based on a pre-defined model, which may be a heuristic or a statistical model. This heuristic or statistical model is another instance than the model used for detecting the firing. For example, when lost samples are used for detection, the detection heuristic will contain lost samples, while the reconstructing heuristic model will fill in those missing samples.

According to a sixth option which can be combined with any one of the above first to fifth options, the output signal may be processed based on an external trigger signal, thus constraining detection to particular time spans. The external trigger may for instance be received from a robotic surgery device. This allows use of the proposed system in robotic biopsy.

It is noted that the above medical system may be implemented based on discrete hardware circuitries with discrete hardware components, integrated chips, or arrangements of chip modules, or based on signal processing devices or chips controlled by software routines or programs stored in memories, written on a computer readable media, or downloaded from a network, such as the Internet.

It shall be understood that the medical system of claim 1, the detection method of claim 14, and the computer program product of claim 15 may have similar and/or identical preferred embodiments, in particular, as defined in the dependent claims.

It shall be understood that a preferred embodiment of the invention can also be any combination of the dependent claims or above embodiments with the respective independent claim.

These and other aspects of the invention will be apparent from and elucidated with reference to the embodiments described hereinafter.

DETAILED DESCRIPTION OF EMBODIMENTS

Embodiments of the present invention are now described based on an IGIT tracking system for transperineal biopsies using a biopsy gun. According to various embodiments, it is proposed to use additional processing algorithms to enable tracking of EM sensors moving in distinct, very fast patterns.

Figure 1:
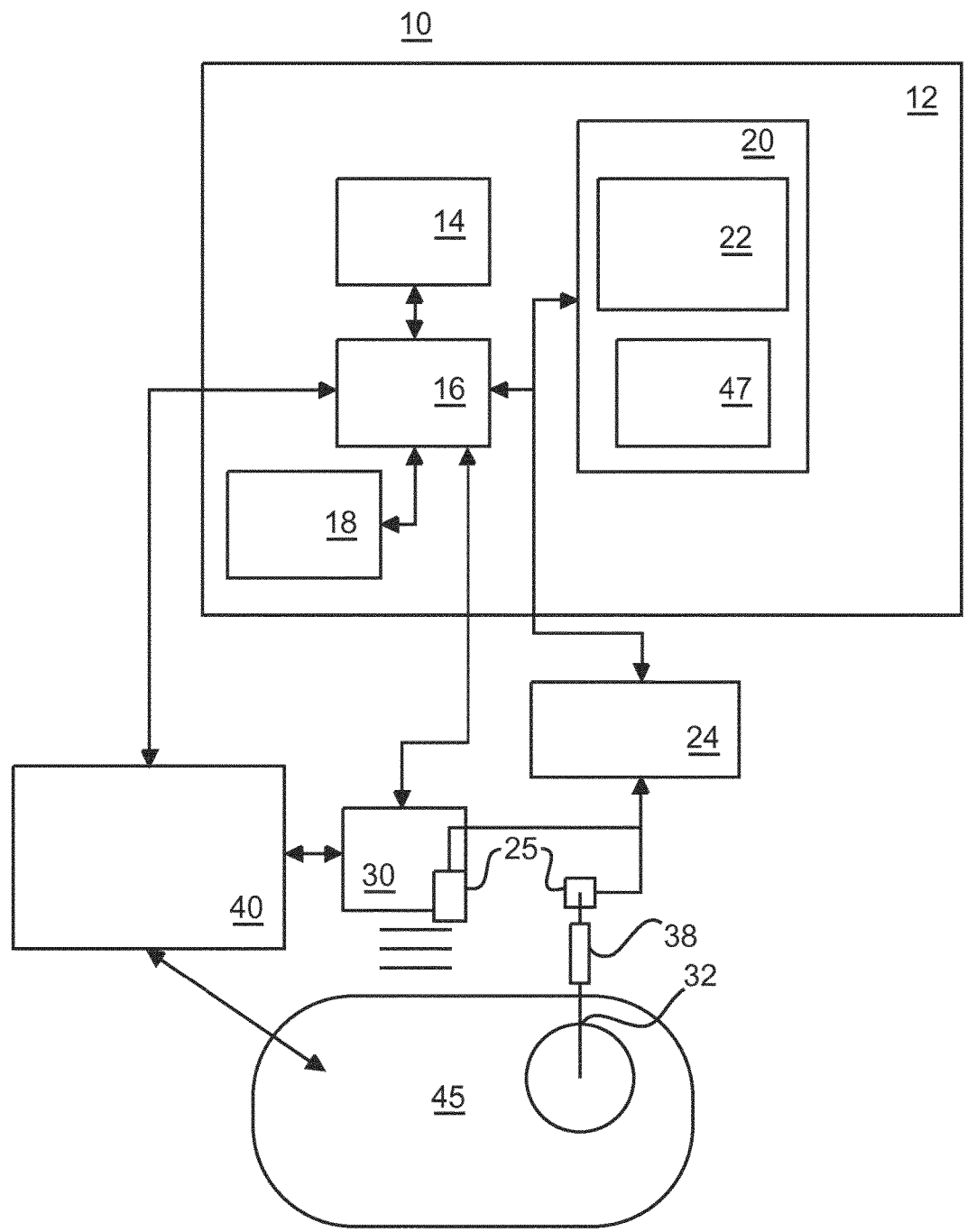
FIG. 1 shows a schematic block diagram of a medical system for integrating surgical device guidance and deployment detection according to various embodiments.

FIG. 1 shows a schematic block diagram of a medical system 10 for integrating needle guidance for biopsies with automatic needle deployment detection and recording according to various embodiments. The medical system 10 may be applied in a variety of clinical procedures, e.g., in image-guided biopsies. In particular, the medical system 10 may assist in automatically documenting a number, time, and location of biopsies performed under image-guided navigation systems on a patient 45. The medical system 10 includes a workstation or computer device 12 that provides planning, navigation and feedback information to a user using, e.g., a display 14. The workstation 12 may include a computer processor 16, the display 14, a user interface 18 (e.g., mouse, keyboard, etc.) and a memory 20 for storing data and software. The memory 20 includes software, which may include a coordination module 22 configured to coordinate image information, spatial tracking data, etc. with medical instrument motion and events associated with the treatment of a subject. According to FIG. 1, a position of an ultrasonic probe 30 and a biopsy needle 32 are concurrently tracked. Biopsy positions are determined using image guidance and recorded with reference to a medical image or images. Furthermore, a spatial tracking system 24 and tracking device 25 may be employed to determine a probe position relative to a medical image. For example, a 6 degree-of-freedom electromagnetic (EM) tracking sensor can be placed on the probe 30 as the tracking device 25. The coordination module 22 collects data indicating a position of a deployment guidance system 38 (such as a needle guide, biopsy gun or other device), a biopsy needle 32, or any other instrument. The deployment guidance system 38 is instrumented to provide deployment detection of motion of the biopsy needle 32 and/or triggering (e.g., collection of a sample). Furthermore, the coordination module 22 coordinates integration of automatic instrument deployment detection, position determination and recording. The detection may be based on images, e.g., transrectal ultrasound images/ video stream, collected from an imaging device 40. A filter 47 can be employed to assist in tracking the biopsy needle 32 with an image of the subject 45. Furthermore, the detection can be based on spatial tracking data from the tracking device 25, e.g., from a tracked biopsy needle 32 and/or probe 30. Using one or more of these devices, at least the time and location of events (biopsy sample) can be determined within the subject 45. The detection of deployment operations of the biopsy needle 32 may be correlated with a reference coordinate system so that time and location of, e.g., biopsy sample, may be recorded for future reference.

Figure 2:
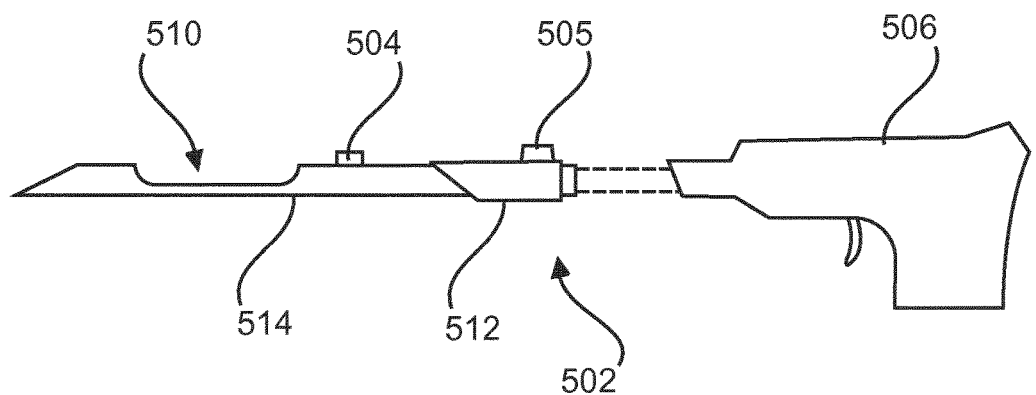
FIG. 2 shows a schematic structure of a biopsy gun and needle having a stationary tracking device and a moving tracking device on the needle.

FIG. 2 shows a schematic structure of a biopsy gun 506 and a biopsy needle 502 having a stationary tracking device and a moving tracking device on the biopsy needle 502. A needle deployment can be automatically detected, and a location of a biopsy core 510 can be determined by spatial tracking of the biopsy needle 502. For that purpose, an EM tracking sensor or sensors 504 or 505 are provided on the biopsy gun 506 and can be attached either on a "stationary" or on a "moving" reference point of the biopsy needle 502. The stationary reference point does not move relative to a needle shaft when the biopsy gun 506 is fired. The stationary reference point may be located on an outer needle or cannula 512 of the needle 502. A moving reference point moves forward along a needle axis with a needle deployment mechanism when the biopsy gun 506 is fired. The moving reference point may be located on an inner needle or trocar 514 of the needle 502.

In particular, the signal from the tracking sensor 504 on a "moving" point of the biopsy needle 502 can be used directly to detect the deployment of the biopsy needle 502, and to record its location.

The biopsy gun 506 usually contains a grip incorporating a spring-loading or other acceleration mechanism that drives the trocar 514 and the cannula 512 of the biopsy device. Upon releasing a first spring, the trocar 514 is driven into the tissue (the armed state), while releasing a second spring drives the cannula 512 forward to encapsulate the tissue sample (the fired state).

The biopsy device in which embodiments of the present invention can be applied has at least one EM sensor embedded in the trocar 514, or the cannula 512.

Figure 3:
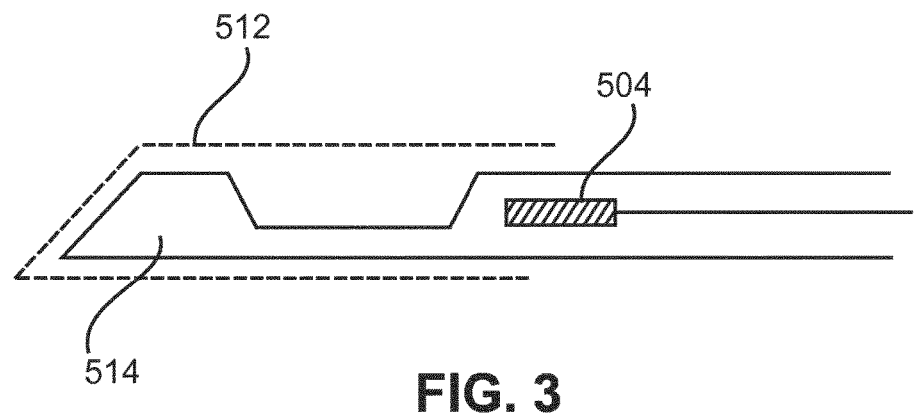
FIG. 3 shows a schematic structure of a biopsy needle tip with an integrated EM sensor.

FIG. 3 shows a schematic structure of a tip of a biopsy needle with an integrated EM sensor 504 with a lead wire for connection to a tracking device. The EM sensor 504 is fixed to the trocar 514 to ensure that it measures movements when the biopsy gun is fired. An alternative implementation is to integrate the EM sensor in the cannula 512, which also moves when the biopsy gun is fired. In FIG. 3, the stippled line illustrates the trocar 514 being surrounded at the needle tip by the cannula 512 (i.e., now depicting a fired state compared to a pre-fired state in which the trocar 514 has been driven into the tissue of the subject).

Figure 4:
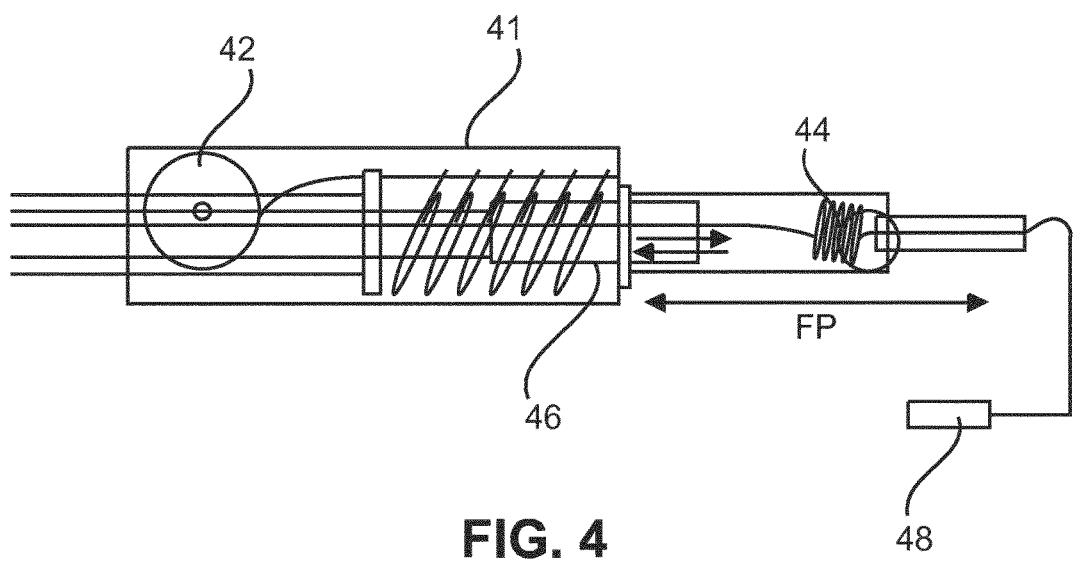
FIG. 4 shows a schematic structure of a biopsy gun housing with a cable to allow trocar movement.

FIG. 4 shows a schematic structure of a biopsy gun housing 41 with a cable to allow trocar movement. An outer tube 46 moves with the inner tube of the biopsy gun. Furthermore, an over length of the cable or lead wire of the EM sensor 504 of FIG. 3 is wound in a spiral 44 in a fixed part (FP) of the biopsy gun to allow movement of the lead wire. The other (outer) end of the lead wire connected to a cable of a circular push-pull connector (e.g. Redel® connector) 48. Furthermore, a release button 42 is provided, which when pushed for a first time will make the trocar move forward, and when pushed for a second time, this will make the cannula move forward.

As intended, the biopsy device can now be tracked while the needle is being positioned in preparation of the actual biopsy taking. However, when taking a biopsy, the spring loading mechanism drives the trocar into the tissue at high speed to reduce deformations and trauma, resulting in a temporary loss of the EM signal. The previously envisaged biopsy detection thus fails when using a straightforward implementation due to the earlier described problems with tracking fast moving sensors.

According to the embodiments, additional processing algorithms are introduced to allow processing the signals from the fast moving EM sensors. These algorithms incorporate dedicated prior knowledge or information on the expected signal obtained from the trocar-embedded or cannula-embedded EM sensor when the spring-loaded mechanism fires. Such prior information used in the additional processing may comprise at least one of a fact that the signal is lost in itself, a number of samples during which the signal is lost (this may include lost signals due to actual motion, as well as recovery time due to recursive filtering of the EM system), a translation distance between the points before and after losing signal, and orientation alignment between points before and after losing signal.

Figure 5:
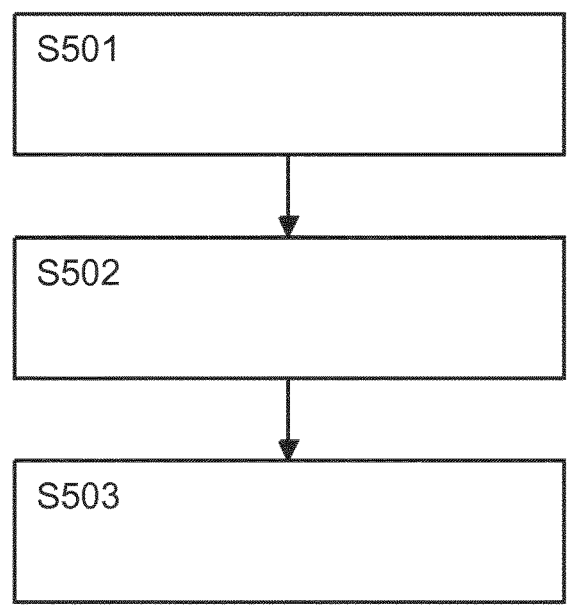
FIG. 5 shows a flow diagram of a tracking signal processing procedure according to a first embodiment.

FIG. 5 shows a flow diagram of a tracking signal processing procedure according to a first embodiment where the above prior information is incorporated in a heuristic algorithm or descriptor to process the EM signal. The procedure may be executed by the processor 16 of FIG. 1.

In step S501 prior information is derived from a detected sensor output. Then, in step S502, this prior information is incorporated in a heuristic model or descriptor. Generally speaking, a heuristic is a rule of thumb, an order of magnitude, a factor of safety, or a good guide to follow when making decisions. Therefore, a heuristic process may include running tests and getting results by trial and error. As more sample data is tested, it becomes easier to create an efficient algorithm to process similar types of data. These algorithms are not always perfect, but work well most of the time. The goal of heuristics is to develop a simple process that generates accurate results in an acceptable amount of time. The heuristic model can be based on any properties that can be measured using the EM system. As a non-limiting example, a fast movement could be described as a movement (e.g. 20 mm) along a measured orientation with a predetermined number (e.g. 3) of samples signal loss in between. This description is called a heuristic model, or heuristic descriptor, where the movement distance and number of samples are parameterizations that are set by trial and error. A processing method detecting a fast movement based on such kind of description can be referred to as a heuristic algorithm.

Such a heuristic approach can be parameterized to cover a class of similar devices. E.g., the expected translation distance can be a parameter, to deal with variations in the translation distance between different types of biopsy devices. To enable the use of different biopsy devices within the same IGIT solution, these parameter values can be modifiable from the user interface of the system (e.g. user interface 18 of FIG. 1), or through a configuration mechanism. As a non-limiting example, for one biopsy gun, the movement distance may be 20 mm, for another 25 mm. The heuristic descriptor is then said to have a parameter "movement distance". The parameter may be configurable in the graphical user interface, configuration files, etc. of the hosting system.

Finally, in step S503, the output signal of the EM sensor provided on the trocar is processed based on the heuristic model or descriptor to recover lost portions or the whole signal output.

Figure 6:
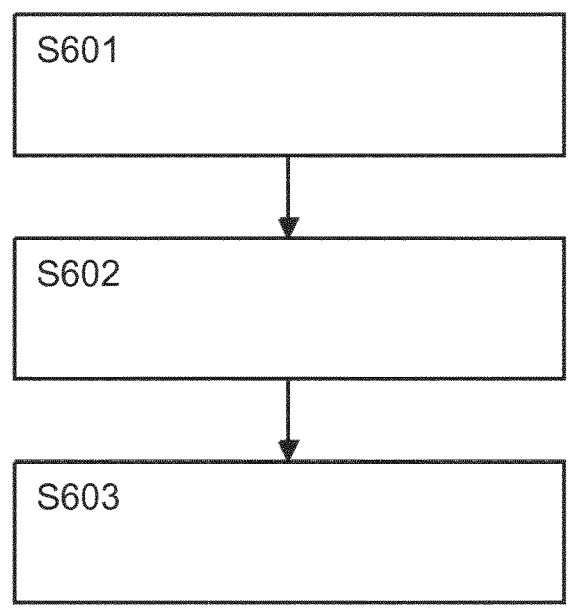
FIG. 6 shows a flow diagram of a tracking signal processing procedure according to a second embodiment.

FIG. 6 shows a flow diagram of a tracking signal processing procedure according to a second embodiment, which may be executed by the processor 16 of FIG. 1.

In the alternative implementation of the second embodiment, a statistical model is built for the EM signal that is expected when firing the biopsy gun. In step S601, the EM signal is recorded while firing the biopsy device a number of times, to obtain prior knowledge or information. Then, in step S602, a statistical descriptor or model is calculated or determined based on the prior information. The statistical model relates signal samples before and after signal loss. Again, to enable the use of different biopsy devices within the same IGIT solution, a statistical training procedure can be available through a user interface of the system, e.g. user interface 18 of FIG. 1. Finally, in step S603, the output signal of the EM sensor provided on the trocar is processed based on the statistical model or descriptor to recover lost portions or the whole signal output. As a non-limiting example, an EM tracked biopsy device may be fired for 50 times. The obtained EM signals are temporally aligned, and processed using e.g. a principal component analysis, resulting in the average signal, as well as modes of variations. This is the statistic model obtained from the training stage. Now, this statistical model can be used when performing biopsies. Upon receiving each EM sample, the system will evaluate whether the last samples fit within the variation of the statistical model. If the samples do fit, a device firing is detected.

So far, the described implementations may still produce a number of false positive device firing detections, where signal loss is due to moving the biopsy device out and in the tracking volume or due to (re-)connecting EM devices. These false positives may be suppressed by extending the heuristic approach of the first embodiment. In such a case, the fact that the EM tracking system reports a state with each sample can be used. In this state field, missing and out-of-volume are different values. The naive heuristic approach ignores this state field, and detects a biopsy gun firing purely based on the motion pattern. The extended heuristic approach uses the state field, such that detection is suppressed if the device is moved outside the tracking volume. As another option, the false positives can be made part of the recording of an EM signal that is used to train the statistical descriptor (adding such examples will improve the robustness of the statistical descriptor). It is noted that a statistical detector can also be complemented by a heuristic false positive suppression.

Once the biopsy device firing is detected, it is also possible to reconstruct the lost signal based on previously defined motion pattern.

If motion of the EM sensor is fast, but not fast enough for complete signal loss, a milder form of the problem occurs. The inaccurate tracking information during movement causes false negatives in straightforward implementations.

Potential applications are anticipated when the EM tracking is used to control robotic surgery. For instance, needle placement by means of a robotic device (e.g. a robot) operating an EM tracked needle may suffer from the same problem. In this particular scenario, both the heuristic or statistic approach may be extended by using an external trigger coming from the robotic device.

To summarize, an EM tracking technology has been described, that can be used to track devices with embedded EM sensors over time. If these objects move too fast, tracking signals are lost because of the motion induced potential differences. It is therefore proposed to add a processing mechanism incorporating additional processing algorithms to enable tracking of the EM sensors. An embodiment of the invention is for performing biopsies using a biopsy gun. The additional processing algorithms incorporate dedicated prior information on the expected signal obtained from the embedded EM sensor and are introduced to allow processing the signals from the moving sensors. The prior information can be incorporated in a heuristic or statistical model to process the EM signal.

While the invention has been illustrated and described in detail in the drawings and foregoing description, such illustration and description are to be considered illustrative or exemplary and not restrictive. The invention is not limited to the disclosed embodiments. The proposed processing can be applied to all IGIT systems or other medical systems that use electromagnetic tracking, in particular those that support biopsy taking, such as transrectal prostate biopsies or transperineal biopsies, or navigation by tracked instruments.

Other variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage.

The foregoing description details certain embodiments of the invention. It will be appreciated, however, that no matter how detailed the foregoing appears in text, the invention may be practiced in many ways, and is therefore not limited to the embodiments disclosed. It should be noted that the use of particular terminology when describing certain features or aspects of the invention should not be taken to imply that the terminology is being re-defined herein to be restricted to include any specific characteristics of the features or aspects of the invention with which that terminology is associated.

A single unit or device may fulfill the functions of several items recited in the claims. The mere fact that certain measures are recited in mutually different dependent claims does not indicate that a combination of these measures cannot be used to advantage.

The described operations like those indicated in FIGS. 5 and 6 can be implemented as program code means of a computer program and/or as dedicated hardware. The computer program may be stored and/or distributed on a suitable medium, such as an optical storage medium or a solid-state medium, supplied together with or as part of other hardware, but may also be distributed in other forms, such as via the Internet or other wired or wireless telecommunication systems.

The invention claimed is:

1. A medical system incorporating an automatic detection system, comprising:
    a guidance system having an acceleration mechanism for generating an accelerated movement of a surgical device to drive the surgical device into a tissue of a subject;
    an electromagnetic sensor provided on the surgical device;
    an electromagnetic spatial measurement system adapted to detect an induced output signal of the electromagnetic sensor and to determine at least one of an orientation and a location of the surgical device based on the detected output signal; and
    a signal processing unit adapted to process the detected output signal and detect an activation of the acceleration mechanism based on a loss of the output signal due to the accelerated movement of the surgical device and dedicated prior information about the output signal of the electromagnetic sensor that is expected when the acceleration mechanism is activated.

2. The medical system of claim 1, wherein the signal processing unit is adapted to process the detected output signal by incorporating the prior information in a heuristic descriptor.

3. The medical system of claim 2, wherein the signal processing unit is adapted to process the detected output signal based on at least one of a fact that the output signal is lost, a number of samples that the output signal is lost, a translation distance between location points before and after losing the output signal, and an orientation alignment between the location points before and after losing the output signal.

4. The medical system of claim 2, wherein the signal processing unit is adapted to parameterize the heuristic descriptor to cover at least one class of similar devices.

5. The medical system of claim 2, wherein the medical system comprises a user interface or a configuration mechanism adapted to allow configuration of parameter values of the heuristic descriptor.

6. The medical system of claim 1, wherein the signal processing unit is adapted to generate a statistical model for the output signal as expected when the acceleration mechanism is activated.

7. The medical system of claim 6, wherein the statistical model relates to one or more samples of the output signal before and after the output signal is lost, including lost samples.

8. The medical system of claim 6, wherein the signal processing unit is adapted to record the output signal a plurality of times in response to the activation of the acceleration mechanism so as to compute the statistical model.

9. The medical system of claim 6, further comprising a training user interface for modifying the statistical model in accordance with different types of the surgical device.

10. The medical system of claim 1, wherein the signal processing unit is adapted to process the detected output signal based on a previously defined motion pattern.

11. The medical system of claim 10, wherein the signal processing unit is adapted to reconstruct a lost output signal based on a pre-defined model.

12. The medical system of claim 1, wherein the signal processing unit is adapted to process the detected output signal based on an external trigger signal received from a robotic surgery device.

13. The medical system of claim 1, wherein the medical system is an image guided interventions and therapy, IGIT, system for detecting placement of a biopsy device.

14. The medical system of claim 1, wherein the signal processing unit is adapted to detect the activation of the acceleration mechanism is based on a reported state from the electromagnetic spatial measurement system.

15. A detection method, comprising:
    generating an accelerated movement of a surgical device to drive the surgical device into a tissue of a subject, by using an acceleration mechanism;
    detecting an induced output signal of an electromagnetic sensor provided on said surgical device;
    determining at least one of an orientation and a location of the surgical device based on the detected output signal; and
    processing the detected output signal and detecting an activation of the acceleration mechanism based on a loss of the output signal due to the accelerated movement of the surgical device and dedicated prior information about the output signal of the electromagnetic sensor that is expected when the acceleration mechanism is activated.

16. A non-transitory computer program product comprising code means for producing the steps of claim 15 when run on a computer device.

* * * * *